(12) United States Patent
Portman

(10) Patent No.: US 6,838,431 B2
(45) Date of Patent: Jan. 4, 2005

(54) NUTRITIONAL INTERVENTION COMPOSITION CONTAINING A SOURCE OF PROTEINASE INHIBITOR EXTENDING POST MEAL SATIETY

(75) Inventor: Robert Portman, Fair Haven, NJ (US)

(73) Assignees: Pacific Health Laboratories, Inc.; Kemin Consumer Care, L.C.

( * ) Notice: Subject to any disclaimer, the term of this patent is extended or adjusted under 35 U.S.C. 154(b) by 103 days.

(21) Appl. No.: 10/085,355

(22) Filed: Feb. 28, 2002

(65) Prior Publication Data

US 2002/0119915 A1 Aug. 29, 2002

Related U.S. Application Data

(63) Continuation-in-part of application No. 09/624,922, filed on Jul. 25, 2000, now abandoned, and a continuation-in-part of application No. 09/626,207, filed on Jul. 26, 2000, now abandoned.
(60) Provisional application No. 60/145,892, filed on Jul. 27, 1999.

(51) Int. Cl.$^7$ .......................... C07K 14/00; A01N 37/18
(52) U.S. Cl. ........................... 514/2; 514/773; 514/775; 514/780; 514/783; 530/360; 530/370; 426/590
(58) Field of Search ........................... 514/2, 773, 775, 514/780, 783; 530/370, 360; 426/590

(56) References Cited

U.S. PATENT DOCUMENTS

| | | |
|---|---|---|
| 4,491,578 A | 1/1985 | Peikin |
| 4,833,128 A | 5/1989 | Solomon et al. |
| 5,086,042 A | 2/1992 | Rosamond |
| 5,221,668 A | 6/1993 | Henningfield et al. |
| 5,340,603 A | 8/1994 | Neylan et al. |
| 5,468,727 A * | 11/1995 | Phillips et al. ................ 514/12 |
| 5,750,353 A | 5/1998 | Kopin et al. |
| 5,814,316 A | 9/1998 | Cook et al. |
| 5,827,517 A | 10/1998 | Cook et al. |
| 5,932,561 A | 8/1999 | Meyers et al. |
| 5,989,584 A | 11/1999 | Cook et al. |
| 6,355,612 B1 | 3/2002 | Ballevre et al. |
| 6,429,190 B1 * | 8/2002 | Portman ........................ 514/2 |
| 6,436,899 B2 * | 8/2002 | Portman ........................ 514/2 |

OTHER PUBLICATIONS

Calam J. Bojarski JC and Springer CJ. Raw soybean flour increases cholecystokinin release in man. *Br J of Nutr* 58:175–179, 1987., Abstract only.
Debas HT, Farooq O and Grossman MI. Inhibition of gastric emptying is a physiological action of cholecystokinin. *Gastroenterology* 68:1211–1217, 1975., Abstract only.
Dlugosz J. Folsch VR and Creutzfeldt W Inhibition of intraduodenal typsin does not stimulate exocrine pancreatic secretion in man. *Digestion* 26:197–204, 1983., Abstract only.
Geracioti TA Jr, Liddle RA. Impaired cholecystokinin secretion in bulimia nervosa. *N Engl J Med* 319:683–688, 1988., abstract only.
Gibbs J, Falasco JD and McHugh PR. Cholecystokinin–decreased food intake in Rhesus monkeys. *Am J Physiol* 230:15–18, 1976.
Green GM and Lyman RL. Chymotrypsin inhibitor stimulation of pancreatic enzyme secretion in the rat. *Proc Soc Exp Biol Med* 136:649–654, 1971.
Green GM and Lyman RL. Feedback regulation of pancreatic enzyme secretion as a mechanism for trypsin inhibitor–induced hypersecretion in rats. *Proc Soc Exp Biol Med* 140:6–12, 1972.
Hill AJ, Peikin SR, Ryan CA, Blundell, JE. Oral administration of proteinase inhibitor II from potatoes reduces energy intake in man. *Physiol Behav* 48(2):241–246, 1990.
Kissileff HR, Pi–Sunyer HR, Thornton I and Smith GP: C–terminal octapeptide of cholecystokinin decreases food intake in man,*Am J Clin Nutrition* 34:154–60, 1981., Abstract only.
Pi–Sunyer X, Kissileff HR, Thornton J and Smith GP. C–terminal octapeptide of Cholecystokinin decreases food intake in obese men. *Physiol Behav* 29(4) 627–630, 1982.
Stacher G, Bauer H and Steinringer H. Cholecystokinin decreases appetite and activation evoked by stimuli arising from the preparation of a meal in man. *Physiol Behav* 23:325–331, 1979.
Stacher, G; Steinringer, H.; Schneider, C.; Winklehner, S. Cholecystokinin octapeptide decreases intake of solid food in man. *Peptides* 3:2, 133–136, 1982., abstract only.
Bryant, Proteinase Inhibitor II from Potatoes: Isolation and Characterization of Its Promoter Components, Biochemistry, vol. 15, No. 16 34 18–24, 1976.
McCarthy, Complementary Measures for Promoting Insulin Sensitivity In Skeletal Muscle, Medical Hypotheses, vol. 51(6), p451–464, 1998., abstract only.
Campbell, Effects of Resistance Training and Chromium Picolinate on Body Composition and Skeletal Muscle in Older Men, Journal of Applications of Physiology, vol. 86(1). p29–39, 1999., abstract only.

(List continued on next page.)

*Primary Examiner*—Jon P. Weber
*Assistant Examiner*—Chih-Min Kam
(74) *Attorney, Agent, or Firm*—Gibbons, Del Deo, Dolan, Griffinger and Vecchione

(57) ABSTRACT

The invention relates to a nutritional intervention composition in powder form that is taken before a meal and that extends post meal satiety. The compositions of the invention are comprised of at least one protein, $C_{12-18}$ fatty acids, preferably oleic acid, all of which stimulate CCK release in the body, and a source of proteinase inhibitor which acts to prevent the deactivation of CCK. The subject compositions preferably additionally contain a source of calcium and are advantageous in that they utilize a source of proteinase inhibitor as opposed to the more costly extracts. The source of proteinase inhibitor is advantageously an extract of potato, soy, or beans containing about 10 weight percent of proteinase inhibitor. The powder compositions are mixed with a suitable liquid, preferably water, prior to ingestion.

9 Claims, 2 Drawing Sheets

OTHER PUBLICATIONS

Spiegel, Effect of a Premeal Beverage Containing a Protease Inhibitor from Potatoes on Satiety in Dieting Overweight Women (unpublished abstract)., abstract only.

Vasselli, Consumption of a Pre-Meal Drink Containing Pretease Inhibitor from Potatoes Decreases Hunger and Increases Fullness in Overweight Subjects Following a Meal (unpublished abstract).

Dawson-Hughes B., Dallal G.E., Krall, E.A, Sadowski, L., Sahyoun N., Tannenbaum, S., A Controlled Trial of the Effect of Calcium SupPlementation on Bone Density in Postmenopausal Women. N Engl J Med., 1990 Sep. 27;323(13):878-83.

* cited by examiner

NUTRITIONAL INTERVENTION COMPOSITION CONTAINING A SOURCE OF PROTEINASE INHIBITOR EXTENDING POST MEAL SATIETY

RELATED APPLICATIONS

This is a continuation-in-part of Ser. No. 09/624,922, filed Jul. 25, 2000, abandoned, and Ser. No. 09/626,207, filed Jul. 26, 2000, abandoned, which is a continuation of provisional application Ser. No. 60/145,892 filed on Jul. 27, 1999.

FIELD OF THE INVENTION

The present invention relates to a nutritional intervention composition for extending satiety following a meal. More particularly, the nutritional intervention composition includes protein, long chain fatty acids and, preferably, calcium to stimulate the secretion of cholecystokinin (CCK) which is a gastrointestinal peptide hormone and a source of proteinase inhibitor which inhibits deactivating enzymes thereby extending elevated levels of CCK for a longer period of time.

BACKGROUND OF THE INVENTION

Over the last forty years there has been extensive research conducted on mechanisms that would extend satiety following the ingestion of a meal. Compositions that would effectively extend satiety following a meal would be of significant benefit in programs of weight reduction and control. Research into mechanisms for weight loss and control has focused on three areas. Because the brain plays an essential role in the control of appetite, researchers have looked at various neurotransmitters, specifically serotonin, dopamine and nor-epinephrine. A number of prescription and over-the-counter products have been developed which influence these neurotransmitters, thereby reducing appetite. However, reducing appetite pharmacologically has a number of drawbacks, including a decrease in the efficacy of the medication over a period of time. Drugs that affect neurotransmitters also affect the central nervous systems and can cause jitteriness and anxiety. In addition, these agents can produce cardiovascular effects that may have very serious consequences.

A second approach has focused on slowing gastric emptying thereby creating a feeling of fullness. This approach utilizes insoluble fibers, which slow the movement of food through the gastrointestinal tract. The disadvantage in the use of such fiber is that the quantities needed to produce the desired effect create an unpalatable diet as well as numerous gastrointestinal side effects including bloating, gas and diarrhea.

A third approach has focused on means of stimulating the body's satiety mechanism. Cholecystokinin (CCK) is a peptide released following the consumption of food. It is reported in the literature that an injection of CCK in animals elicited the total range of satiety behavior. When food is consumed, a peptide is released called Cholecystokinin Releasing Protein (CCK-RP). Cholecystokinin Releasing Protein stimulates the release of cholecystokinin in the gut which, in turn, increases satiety. When cholecystokinin is released, it also stimulates the release of enzymes that inactivate CCK-RP. The inactivation of CCK-RP causes the level of CCK to drop and, therefore, diminishes the feeling of satiation. Studies have shown that CCK is extremely effective in extending satiety following ingestion of a meal. Although CCK has been shown to extend satiety and reduce food intake, a major disadvantage is that it must be given intravenously because it is inactivated by gastric enzymes upon oral administration. This has severely limited its use as a potential weight loss agent.

Release of cholecystokinin has also been shown to be a satiety signal in humans. In 1981, researchers demonstrated that an injection of CCK decreased food intake by 16 percent. The subjects did not alter their rate of eating, but rather stopped eating sooner, which would be the expected result if cholecystokinin were a satiety signal. The results in humans confirmed the laboratory findings that CCK is an important agent in terminating the meal. CCK levels in man peak within 20 minutes following a meal and usually return to baseline in about one hour. Although the full mechanism whereby CCK exerts its effect on satiety is not known, there appears to be two components, a central component involving CCK receptors in the brain and a peripheral component involving the stomach and small intestine.

When food is consumed, CCK releasing protein (CCK-RP) is released in the small intestine. CCK-RP stimulates CCK release from intestinal cells. The release of CCK generates the behavioral symptoms associated with satiety and at the same time stimulates the pancreas to secrete a number of proteases, specifically trypsin and chymotrypsin, which inactivate CCK-RP. When trypsin and chymotrypsin are inactivated by addition of a proteinase inhibitor, the inactivation of CCK-RP is prevented thereby sustaining the levels of CCK. Studies have shown that proteinase inhibitor extracted from potatoes stimulates the release of CCK. The ability of CCK to reduce appetite would appear to make it an extremely useful agent in treating obesity. In a weight management program, stimulation of CCK would result in a reduction of hunger cravings between meals. These effects would enable an overweight individual to better comply with a diet that requires a reduced caloric intake. The literature has shown that CCK release can be stimulated by protein, calcium and long chain fatty acids.

A number of nutritive agents can stimulate the release of cholecystokinin. Researchers have shown that protein, fat (particularly medium chain fatty acids), and calcium stimulate the release of CCK. The literature has also shown that oral administration of a proteinase inhibitor from potatoes produced a marginal decrease in energy intake when administered with a small amount of carbohydrate. A subsequent study showed that when a proteinase inhibitor (1.5 grams) was combined with dietary protein (15.5 g) and a small amount of unspecified fat (0.7 g), the composition decreased energy intake. However, there was no statistically significant difference compared to the control in subjective ratings of hunger and fullness at 3 hours. Thus, the study shows that this mixture did not provide an extended effect on post meal satiety. Post meal satiety is defined as the interval between meals during which a subject is satiated and there is no food intake.

Increasing post meal satiety in a cost effective manner would be an important benefit in helping an individual lose weight by lengthening the interval between meals thereby reducing additional consumption of calories. There is a definite need in the art for a cost effective, safe nutritional intervention composition that can be taken orally. Since proteinase inhibitor is expensive to extract and purify from potatoes, it follows that it would be a decided advantage for such a nutritional composition to take advantage of the positive effect of a proteinase inhibitor yet reduce the amount of proteinase inhibitor required to produce that effect.

Compositions that stimulate satiety are known. U.S. Pat. No. 4,833,128 discloses the oral administration of phenylalanine in conjunction with protein, carbohydrate and fat to stimulate satiety. It is disclosed that when a dietary supplement containing phenylalanine is consumed fifteen minutes prior to a meal, it generates a feeling of satiety resulting in reduced food consumption. However, the presence of phenylalanine in the disclosed preparations limits their use in patients with phenylketonuria. Finally, the patent makes the statement, alluding to a literature citation, that the appetite suppression of CCK may be merely temporary resulting in a limited satiety effect, possibly followed by a "rebound" of weight gain.

U.S. Pat. No. 4,491,578 discloses the oral administration of a trypsin inhibitor to enhance satiety by stimulating the release of CCK. This patent teaches that the negative feedback signal for cholecystokinin secretion results from the release of trypsin from the pancreas. The administration of a therapeutically effective quantity of trypsin inhibitor blocks the trypsin released from the pancreas thereby interfering with a negative feedback mechanism. The disclosed composition relies solely on a trypsin inhibitor to stimulate CCK whereas both trypsin and chymotrypsin are involved in inactivating CCK-RP and in fact it has been shown that chymotrypsin plays a more important role inhibiting CCK release. The composition only blocks trypsin, whereas the nutritional intervention composition of the present invention includes proteinase inhibitors that block trypsin as well as chymotrypsin, thus providing more effective CCK release in humans.

There is a definite need in the art for a nutritional intervention composition that can be taken orally, stimulate cholecystokinin levels prior to the initiation of a meal and sustain cholecystokinin levels and satiety for an extended period following consumption of a meal. There is a further need in the art for a nutritional intervention composition that works with proteinase inhibitor to provide a greater release of CCK resulting in an extended effect on post meal satiety. Such compositions are provided in accordance with the present invention.

SUMMARY OF THE INVENTION

In accordance with the present invention, there is provided a nutritional intervention composition in powder form that is taken prior to a meal and extends satiety after a meal in a fashion that is efficient in terms of the number of added calories. The nutritional intervention composition includes one or more proteins, certain long chain fatty acids and a source of proteinase inhibitor, preferably also including a source of calcium. The nutritional intervention composition of the present invention is intended to be mixed with liquids, preferably water, to form a drink prior to ingestion.

BRIEF DESCRIPTION OF THE FIGURES

Further features, and advantages of the present invention will become apparent upon the consideration of the following detailed description of the presently preferred embodiment when taken in conjunction with the accompanying drawings, wherein.

DETAILED DESCRIPTION OF THE INVENTION

Figure 1:
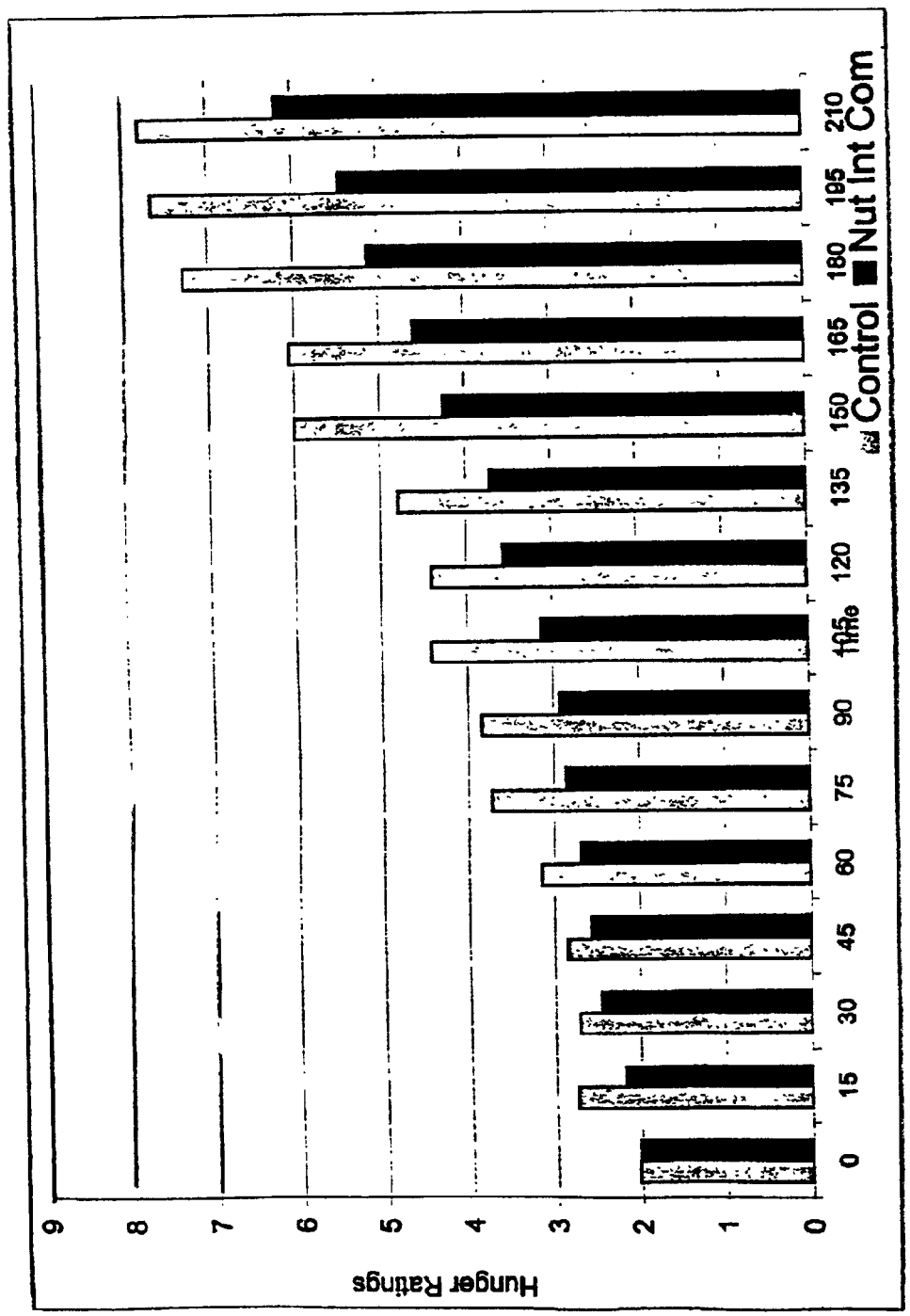
FIG. 1 is a graph showing a comparison of hunger ratings over time between a control beverage and the nutritional intervention composition of the present invention.

The nutritional intervention composition of the present invention is based on the surprising discovery that by combining specific nutritional agents, including one or more proteins, long chain fatty acids with a proteinase inhibitor, preferably further including a source of calcium, satiation following a meal can be extended for up to about 3.5 hours. Further, by combining these nutritional agents with a natural source of proteinase inhibitor, it is possible to achieve this extension of satiety without preparing a purified extract of the proteinase inhibitor, thereby achieving the desired extension of satiety in a cost-effective manner.

The proteinase inhibitor component of the subject compositions is preferably a heat stable protein that may be extracted from potatoes and has a molecular weight of approximately 21,000. The proteinase inhibitor may be added in the form of ground whole potatoes or components of potatoes that include it. Alternatively, the proteinase inhibitor may be sourced from other plant sources, such as soybeans, other beans, and tomatoes. It is both a trypsin and chymotrypsin inhibitor, with its critical functionality being that it stimulates the release of cholecystokinin. A method of extraction of a proteinase inhibitor of the present invention from potatoes is described in Bryant, J., Green, T. R., Gurusaddalah, T., and Ryan, C. A. (1976), *Biochem.* 15, 3418.

The subject nutritional intervention, in addition to the proteinase inhibitor, is comprised of at least one protein and certain long-chain fatty acids, preferably further including a source of calcium, all of which have been shown to stimulate the release of CCK. The subject compositions preferably additionally contain conventional additives such as flavoring ingredients, coloring agents, artificial sweeteners, emulsifiers and the like. The nutritional intervention compositions of the present invention are efficient form a caloric standpoint as they typically have a calorie content of 50 to 150 calories, preferably about 80 calories.

The protein component of the subject compositions may be one or a mixture of essential amino acids, but is preferably one or more of casein, whey and soy proteins. The protein component comprises from about 63 to about 74 weight percent of the subject compositions. The long chain fatty acid component of the subject compositions comprises from about 18 to 25 weight percent and consists of at least one $C_{12-18}$ fatty acid, preferably at least one $C_{18}$ fatty acid, most preferably oleic acid. A preferred composition is predominately, i.e. at least 50 weight percent, oleic acid with the remainder being comprised of other $C_{12-18}$ fatty acids. Sources of oleic acid include babassu oil, butter oil, cocoa butter, coconut oil, safflower oil, soybean oil, palm kernel oil, peanut oil and the like.

The proteinase inhibitor component of the subject nutritional intervention compositions may be a purified extract from a natural source, such as potatoes. However, as stated above, it is preferred for cost considerations that it not be present as a purified extracted material, but as a source of proteinase inhibitor that is commercially available and which, on the average, contains about 10 weight percent of proteinase inhibitor. It is a distinct advantage of the subject compositions that such sources may be utilized with the beneficial effect of the proteinase inhibitor. In addition to potatoes, such sources may be from soy and beans as well. The proteinase inhibitor source is present in an amount sufficient to provide from about 0.16 to about 0.63 weight percent of the purified material. Since the sources contemplated for inclusion in the subject compositions contain about 10 weight percent of the purified material, the subject compositions will comprise from about 1.6 to about 6.3 weight percent of the proteinase inhibitor source The calcium source may be selected from those calcium salts commonly utilized in food and medicinal compositions including, without intended limitation, calcium lactate, calcium carbonate, calcium citrate, calcium maleate, calcium citrate maleate and any suitable equivalent thereof. It is preferred to have the calcium source present as it has been shown to be effective in stimulating CCK release. The source of calcium, if present, comprises from about 3.7 to 4.5 weight percent of the subject compositions.

The nutritional intervention compositions of the present invention may include a flavor component for imparting a characteristic taste thereto consisting of water-soluble, natural or artificial extracts that including, without intended limitation, apple, banana, cherry, cinnamon, cranberry, grape, honeydew, honey, kiwi, lemon, lime, orange, peach, peppermint, pineapple, raspberry tangerine, watermelon, wild cherry and equivalents thereof. The flavor component, if present, typically comprises from about 1.8 to 2.3 weight percent of the compositions.

The subject nutritional intervention compositions may further include a colorant component for imparting a characteristic color to the nutritional intervention composition selected from the group consisting of water-soluble, natural or artificial, dyes of blue, green, orange, red, violet, and yellow; iron oxide dyes, ultramarine pigments of blue, pink, red, and violet and equivalents thereof. The coloring component typically will be present in a sufficient quantity to impart the desired color to a liquid preparation prepared from the subject powder compositions. While this may vary with the individual color, typically less than 0.5 weight percent is utilized to obtain the desired color. Artificial sweeteners, such as aspartane, and emulsifiers suitable for food products, such as lecithin, are each utilized in an amount sufficient to impart its characteristic property to the composition. The artificial sweeteners will typically be present in from about 0.2 to 0.3 weight percent of the subject compositions.

The present invention provides for a nutritional intervention composition in a powder form for extending satiety following a meal. The nutritional agents are protein, long chain fatty acids, calcium, a source of proteinase inhibitor, flavoring agents and coloring agents. The following table illustrates the subject nutritional intervention compositions showing both the amount in grams that might be present in a typical single meal package as well as the weight percent.

|  |  | Range (gm) | | Range (%) | |
| --- | --- | --- | --- | --- | --- |
| Ingredient | Source | Lower | Upper | Lower | Upper |
| Protein | Casein, whey, soy, essential amino acids | 4 | 20 | 63.3 | 74.0 |
| Long chain fatty acids | Oleic acid, C12–C18 fatty acids | 1 | 8 | 18.5 | 25.3 |
| Calcium | Lactate, Carbonate, Citrate | 0.2 | 1 | 3.7 | 4.5 |
| Proteinase Inhibitor[1] | Potato, soy, beans | 0.1 | 2 | 1.6 | 6.3 |
| Flavors |  | 0.1 | 0.5 | 1.8 | 2.3 |
| Artificial sweeteners | Aspartame | 0.01 | 0.1 | 0.2 | 0.3 |
| Total Weight in Grams |  | 5.41 | 31.6 |  |  |

[1]Includes approx. 10% by weight of proteinase inhibitor

The nutritional intervention compositions according to the present invention are to be taken prior to a meal for enhancing satiety before the meal and extending satiety following the meal. By "prior to the meal" is meant typically not more than about thirty minutes prior, preferably not more than fifteen minutes prior to the meal. As a matter of individual preference, some individuals may wish to take the present compositions with the meal, preferable at the beginning thereof. The subject powder compositions are dissolved in or dispersed in a suitable liquid to be administered. While liquids such as skim milk and fruit juices may be utilized, it is preferred that the liquid be water, as it adds no calories to the mixture.

The subject compositions are useful in a program of weight loss and management. Typically, an effective amount of the subject nutritional intervention compositions for a single pre-meal administration comprises from about 5 to 30 grams. Such amounts may be conveniently individually packaged or may be formulated such that they will be readily dispensed using common household measures, e.g. by the teaspoonful or tablespoonful. This amount of powder composition can readily be combined with a conveniently measured amount of liquid, for example, eight ounces of water.

The following experimental results further illustrate the invention, it being understood that they are in no way intended to be limiting thereon.

Experiment 1—Consumption of the Nutritional Intervention Composition of the Present Invention Prior to a Meal Twenty four moderately obese subjects (19 female, 5 male) with a mean age of 43.5 years, body weight equals 87.1 kg (range 63–114) and BMI=31.5 (range 25–39) were randomized in a double blind cross over design. On two separate occasions, the subjects were administered either a control preparation containing polydextrose or one containing the nutritional intervention composition of the present invention. Both compositions were mixed with 8 oz of water and contained 80 calories. Following consumption of either drink, the subjects consumed a meal consisting of 460 g (385 cal) of macaroni and beef casserole. The subjects were permitted fifteen minutes to consume their meal. The subjects were asked to rate their hunger, fullness and thirst using a visual analog scale before and after drinking the beverage, before and after eating the meal and every fifteen minutes for three and one half hours following the meal by answering the following questions:

1. How hungry do you feel right now?
2. How thirsty do you feel right now?
3. How much food would you like to eat right now?

Figure 2:
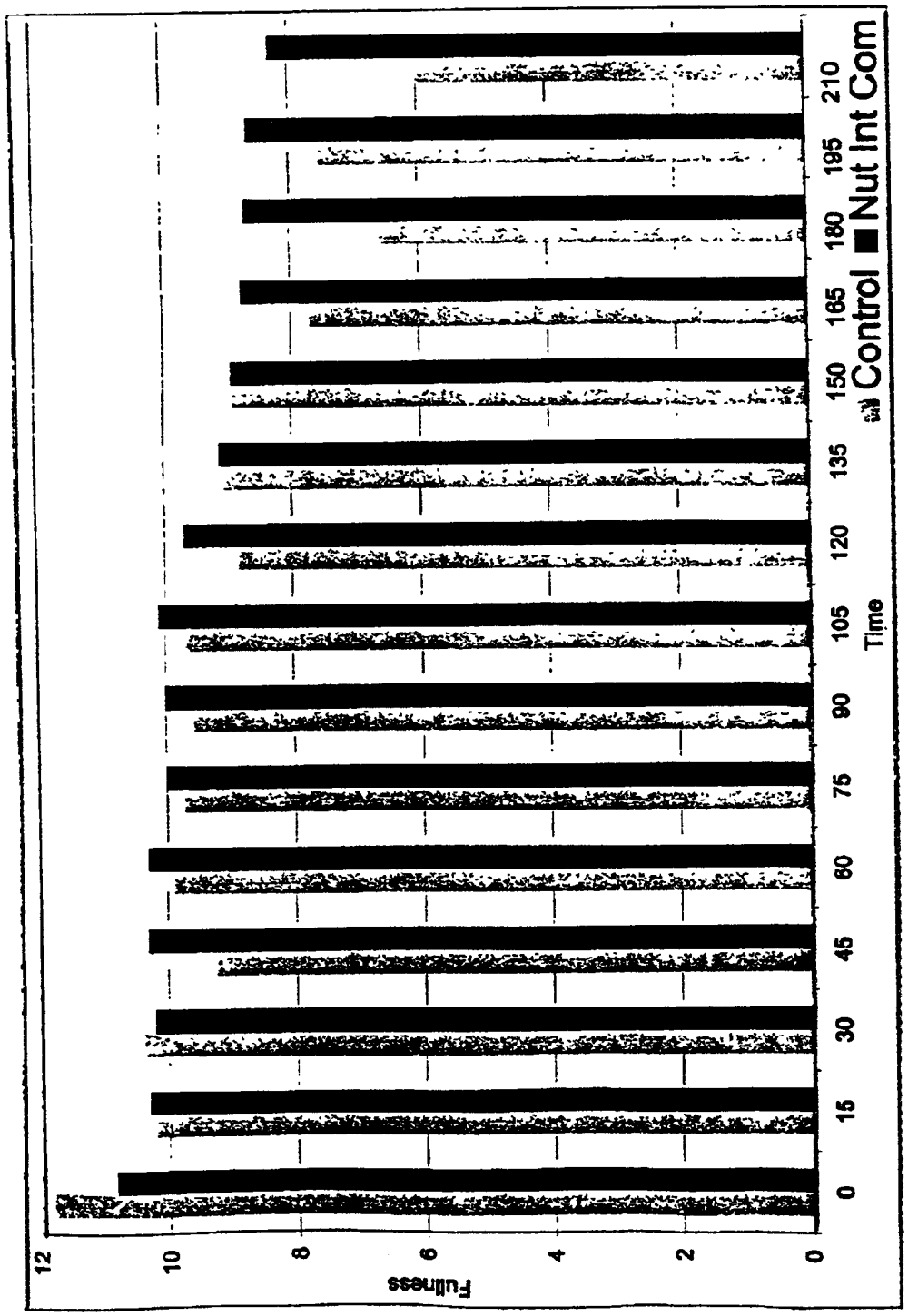
FIG. 2 is a graph showing a comparison of fullness ratings over time between a control beverage and the nutritional intervention composition of the present invention.

A two way repeated measure analysis of variance was used to evaluate the effect of the nutritional intervention composition of the present invention. The results showed:

1. Hunger ratings (FIG. 1) following ingestion of the nutritional intervention composition were significantly decreased throughout the post meal measurement period reaching a 30% decrease by 3 hours post meal (p=0.033).
2. Fullness ratings (FIG. 2) were significantly greater beginning 3 hours post meal showing a 30% increase (p=0.043).
3. No differences in subjective ratings of thirst were observed.

These results demonstrate that consumption of a nutritional intervention composition containing proteinase inhibitor prior to a meal reduced hunger and extended satiety following the meal. The nutritional intervention drink composition of the present of the present invention consumed in the test had the following composition

| Nutritional Drink Composition | | |
|---|---|---|
| Constituent | Grams | Weight Percent |
| Whey Protein | 13.00 | 71.5 |
| Non-Dairy Creamer containing 50% oleic acid | 4.00 | 22.0 |
| Calcium Lactate | 0.67 | 3.7 |
| Flavor | 0.16 | 0.9 |
| Color | 0.04 | 0.2 |
| POT 2[1] | 0.30 | 1.7 |
| Total | 18.17 | 100 |

[1]POT 2 contains approx. 10% by weight of proteinase inhibitor

Experiment 2—Effect of the Nutritional Intervention Composition of the Present Invention on Satiety and Weight Loss over Four Weeks This study was conducted with 21 female subjects having a mean BMI=31.2 (27–35.8) and mean age=30.9. During the diet period, the subjects drank 8 oz. of the nutritional drink composition twice daily, fifteen minutes before lunch and dinner. The effect of the nutritional drink composition on satiety was measured in a laboratory before and in the fourth week of the diet. On one occasion the subjects drank 8 oz of the beverage containing the nutritional intervention composition of the present invention and the control beverage (matched for volume and energy) on the other occasion. Following consumption of either drink, the subjects consumed a standardized meal consisting of approximately 400 calories. The subjects were permitted fifteen minutes to consume their meal. The subjects were asked to rate hunger and fullness using a computer before and after drinking the beverage, before and after eating the meal and every fifteen minutes for three and one half hours following the meal. The subjects were asked to give their ratings to the same questions as set out in the description of Experiment 1.

A two way repeated measure analysis of variance was used to evaluate the effect of the nutritional intervention composition of the present invention. The results of the study show after four weeks:
1. Hunger ratings were 32% lower 3 hours after consuming the nutritional drink composition than the control ($p<0.01$).
2. Fullness ratings were 9% higher after consuming the nutritional drink composition than the control ($p<0.05$).
3. Weight loss was significant, 4.4 lbs in four weeks ($p<0.001$).
4. There were no adverse reactions to the nutritional drink composition.
5. The subjects reported that the nutrition intervention composition helped them reduce their food intake.

These results demonstrate the effectiveness of the present invention over a 30-day period and by extending satiety results in significant weight loss.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A nutritional intervention composition in powder form to be taken before a meal to extend post meal satiety comprising:
   (a) from about 63 to 74 weight percent of one or more proteins that stimulate cholecystokinin (CCK) release, said proteins being selected from the group consisting of casein, whey protein and soy protein;
   (b) from about 18 to 25 weight percent of $C_{12-18}$ fatty acids that stimulate CCK release, said fatty acids comprising at least 50 weight percent oleic acid with the remainder being other $C_{12-18}$ fatty acids that stimulate CCK release; and
   (c) an amount of an extract of potato, soy, or beans containing a proteinase inhibitor to provide from about 0.16 to about 0.63 weight percent of the proteinase inhibitor.

2. The nutritional intervention composition in accordance with claim 1 further including from about 3.7 to 4.5 weight percent of a source of calcium that stimulates CCK release, said source of calcium being selected from the group consisting of calcium lactate, calcium carbonate, calcium citrate, calcium maleate and calcium citrate maleate.

3. The nutritional intervention composition in accordance with claim 1, wherein said extract of potato, soy or beans contains about 10 weight percent of said proteinase inhibitor.

4. The nutritional intervention composition in accordance with claim 1, wherein said composition is mixed with a liquid to form a liquid drink prior to ingestion.

5. The nutritional intervention composition in accordance with claim 4, wherein said liquid is water.

6. The nutritional intervention composition in accordance with claim 1, further including a flavor component for imparting a characteristic taste thereto comprising water-soluble, natural or artificial extracts selected from the group consisting of apple, banana, cherry, cinnamon, cranberry, grape, honeydew, honey, kiwi, lemon, lime, orange, peach, peppermint, pineapple, raspberry, tangerine, watermelon and wild cherry.

7. The nutritional intervention composition in accordance with claim 1, further including a colorant component for imparting a characteristic color thereto comprising water soluble, natural or artificial dyes selected from the group consisting of blue, green, orange, red, violet, and yellow dyes; iron oxide dyes; and ultramarine pigments of blue, pink, red, and violet.

8. The nutritional intervention composition in accordance with claim 1 further characterized in that the calorie content thereof is from about 50 to 150 calories.

9. The nutritional intervention composition in accordance with claim 8, wherein the calorie content thereof is about 80 calories.

* * * * *